US009365887B2

(12) United States Patent
Karlsson et al.

(10) Patent No.: US 9,365,887 B2
(45) Date of Patent: Jun. 14, 2016

(54) RATIONAL ENZYME MINING (75) Inventors: Martin Karlsson, Linköping (SE);
Bengt-Harald Jonsson, Linköping (SE);
Uno Carlsson, Söderköping (SE)

(73) Assignee: RATIONAL ENZYME MINING REM AB, Linkoping (SE)

( * ) Notice: Subject to any disclaimer, the term of this patent is extended or adjusted under 35 U.S.C. 154(b) by 55 days.

(21) Appl. No.: 13/989,513

(22) PCT Filed: Nov. 29, 2011

(86) PCT No.: PCT/SE2011/051449
§ 371 (c)(1),
(2), (4) Date: Jun. 26, 2013

(87) PCT Pub. No.: WO2012/074476
PCT Pub. Date: Jun. 7, 2012

(65) Prior Publication Data
US 2013/0280731 A1 Oct. 24, 2013

(30) Foreign Application Priority Data
Nov. 29, 2010 (SE) ...................................... 1051254

(51) Int. Cl.
*C12Q 1/25* (2006.01)
*C12N 1/36* (2006.01)
*C12Q 1/02* (2006.01)

(52) U.S. Cl.
CPC .. *C12Q 1/25* (2013.01); *C12N 1/36* (2013.01); *C12Q 1/02* (2013.01)

(58) Field of Classification Search
None
See application file for complete search history.

(56) References Cited

FOREIGN PATENT DOCUMENTS

| WO | WO 01/12842 | 2/2001 | ............... C12Q 1/18 |
|----|-------------|--------|--------------------------|
| WO | WO 2004/097001 | 11/2004 | |

OTHER PUBLICATIONS

Ogawa & Shimizu "Microbial enzymes: new industrial applications from traditional screening methods" (Jan. 1999) TibTech: vol. 17: 13-20.*
Wongwilaiwalin et al. "Analysis of a thermophilic lignocellulose degrading microbial consortium and multi-species lignocellulytic ensyme system." (Nov. 8, 2010), vol. 47: 283-290.*
Verma & Madamwar, "Production of Lignolytic Enzymes for Dye Decolorization by Cocultivation of White-Rot Fungi Pleurotus ostreatus and Phanerochaete chrysosporium under Solid-State Fermentation." (2002) vol. 102-103: 109-118.*
Ghazali et al. "Biodegradation of hydrocarbons in soil by microbial consortium" (2004) International Biodeterioration & Biodegradation, vol. 54: 61-67.*
Demain, "Overproduction of Microbial Metabolites and Enzymes Due to Alterations of Regulation" (1971), Avances in Biochemical Engineering vol. 1: 113-142.*
Chen et al. "Purification and identification of cutinases from Colletotrichum kahawae and Colletotrichm gloeosporioides" (2007) Applied Microbiology and Biotechnology: vol. 73: 1306-1313.*
Benndorf et al. "Improving protein extraction and separation methods for investigating the metaproteome of anaerobic benzene communities within sediments." (2009) Biodegradation: vol. 20: 737-750.*
Bobadilla Fazzini et al. "Bacterial consortium proteomics under 4-chlorosalicylate carbon-limiting conditions." (2009) Proteomics, vol. 9: 2273-2285.*
Kovarova-Kovar et al. "Growth Kinetics of Suspended Microbial Cells: From Single-Substrate-Controlled Growth to Mixed-Substrate Kinetics" (1998) Microbiology and Molecular Biology Reviews, vol. 62, No. 3: 646-666.*
Yang et al. "Dynamic and Steady State Studies of Phenol Biodegradation in Pure and Mixed Cultures" (1975) Biotechnology and Bioengineering, vol. 17: 1211-1235.*
Dykhuizen, D. (1993) "Chemostats used for studying natural selection and adaptive evolution" Methods in Enzymnology, vol. 224, pp. 613-631.
Ferrer, M., et al. (2009) "Interplay of metagenomics and in vitro compartmentalization" Microbial Biotechnology, 2(1):31-39.
Ferrer, M., et al. (2009) "Metagenomics for mining new genetic resources of microbial communities" J. Mol. Microbiol Biotechnol, 16:109-123.
Uchiyama, T., et al. (2009) "Functional metagenomics for enzyme discovery: challenges to efficient screening" Current Opinion in Biotechnology, 20:616-622.
International Search Report for PCT/SE2011/051449 dated Mar. 6, 2012.

* cited by examiner

*Primary Examiner* — Robert Yamasaki
*Assistant Examiner* — Teresa E Knight
(74) *Attorney, Agent, or Firm* — Harness, Dickey and Pierce, P.L.C.

(57) ABSTRACT

A method for rational mining for induced enzymes in microbial communities is described. The method is characterized in that a community of microorganisms is provided and that the microbial populations of the community are cultivated in a container under conditions of choice, where the microorganisms are given a defined culturing medium, to eliminate matter deriving from the natural habitat and to allow the microbial community to reach a metabolic steady-state. The method is further characterized in that at least one fraction of microorganisms is taken from the container and transferred into at least two separate containers, where at least one of the fractions of microorganisms is provided with a defined medium which includes an inducing substance and/or a substance against which enzyme/enzymes is/are desired, to induce regulation of expression of the desired enzyme/enzymes, and at least one fraction is provided with a defined medium without said inducing substance and without said substance against which enzyme/enzymes is/are desired, for the purpose of comparison, and the fractions are maintained and/or cultivated. Samples of the two fractions are then withdrawn and analyzed for identification of the induced enzyme/enzymes.

23 Claims, 7 Drawing Sheets

RATIONAL ENZYME MINING

PRIORITY STATEMENT

This application is a national stage application under 35 U.S.C. §371 of PCT International Application No. PCT/SE2011/051449 which has an International filing date of 29 Nov. 2011, and which claims the benefit under 35 U.S.C. §119 to Sweden Application No. 1051254-9 filed 29 Nov. 2010. The contents of each application recited above are incorporated herein by reference in their entirety.

TECHNICAL FIELD OF THE INVENTION

The present invention relates to a method for rational mining for induced enzymes in microbial communities and to a method for mining and production of enzymes. The present invention further relates to an enzyme produced using the methods according to the invention.

BACKGROUND ART

Enzymes are protein biomolecules that are able to function as highly effective, high-performing biological catalysts and are fundamental for all biological life. They are substances that accelerate the chemical reactions of life without being consumed themselves. Isolated enzymes are important in many industrial processes for treating biological substrates. Examples of industries that benefit from the use of enzymes are food and feed industry, detergent industry, leather industry and the increasing application of enzymes in bioenergy industry as exemplified by the production of bioethanol. All the above industries employ various hydrolytic enzymes such as amylases, cellulases, proteases, lipases etc. for increasing production rate and yield of products from biobased feed stock[1]. There are numerous other conceivable applications in related fields e.g. for production of biogas or break down of harmful compounds in process water. Thus, enzymes for industrial and environmental applications have a large and increasing economic and ecological value.

One bottleneck in the application of enzymes in industrial processes is that in order to be active, enzymes and other proteins must keep a highly ordered structure. However, the highly ordered structure of proteins is only maintained if the proteins are stable at the prevailing conditions, i.e. pH, ionic strength, temperature, etc., within certain limits that are specific for each type of protein. In terms of natural selection of proteins during evolution, this notion stresses the fact that a protein molecule only makes structural sense when it exists under conditions similar to those for which it was selected, or the so called, native state. That is, the enzymes for treating biological substrates should ideally be evolutionarily adapted to the environment in which they are to be used, to assure that the enzymes have a high activity and longevity in that unique environment. If however the protein is not stable enough for the application in mind the stability of the enzyme needs to be altered by various protein engineering methods[2], which is a very complex and expensive process with an often uncertain outcome.

Microorganisms are a valuable source of industrially important enzymes. Microorganisms are the smallest form of life, nevertheless they collectively constitute the largest mass of living material on earth. Not only are they the most abundant, but the diversity of microbial life by far exceeds that of the plants and animals, which is a result of microorganisms' ability to live at places unsuitable for other organisms. An ability that comes from microorganisms' highly specialized physiological capabilities. Part of these capabilities comes from having enzymes that are stable, active and adapted to different habitats so that different microorganisms can feed and make use of the nutrients available in different environments.

To feed and utilize nutrition in their environment, microorganisms are generally not able to break down more complex compounds like polysaccharides and proteins within the cell. Their only way to digest them is via extracellular enzymes. For example, to break down starch into glucose the cells secrete amylases into their environment in what could be described as an external digestion process. In the environment the amylases break down starch until the microbes are surrounded by small glucose molecules which can then easily be ingested.

Microorganisms can secrete both cell-bound and free extracellular enzymes. Cell-bound enzymes are important for the microorganisms since they exert their activities close to the microbial cell, which assures that e.g. the glucose produced from the starch can be ingested by the very organism that produced the amylases. For industrial applications however extracellular free enzymes are of larger interest than cell-bound enzymes as they are adapted to be stable independently of the cell and furthermore since the efficiency in degrading complex compounds is far higher for an excreted free enzyme than for a cell-bound one. All microorganisms, both prokaryotic and eukaryotic, have the ability to produce extracellular enzymes. However, for the large scale production of enzymes from isolated genes, prokaryotic enzymes are most often preferred as they lack posttranslational modifications and are thereby easier and cheaper to produce in heterologous expression systems.

Thus, as described above, the large diversity of microorganisms that has evolved in different environments offers an almost inexhaustible bio-bank of organisms with the ability to produce enzymes with different functions in different environments, suitable for various industrial processes. In nature, microorganisms live in association with other microorganisms in populations. The environment in which a population lives is called a habitat in which different populations interact in assemblages called microbial communities. The diversity and abundance of microorganisms in a microbial community is dependent on the resources, i.e. food, and conditions such as temperature, pH, oxygen content etc., that exist in that environment. Microbial habitats can be found in all environments that can sustain life. These includes familiar oxic and anoxic habitats like soil, water, animals and plants but also extreme environments with high or low pH, high or low temperature, high pressure, high salt concentration etc. Following the above reasoning, microorganisms that have evolved to live in any of the above habitats naturally also secrete enzymes that are stable in that very environment.

Microbial populations in a community interact and cooperate in various ways, some of which are beneficial to the whole community. For example, the waste products of metabolic activities of some microorganisms can be nutrients for others. A special case of interaction is syntrophy (literarily meaning "eating together"), a situation in which two or more microorganisms team up to degrade a substance that neither microorganism can degrade individually.

Due to technical limitations, historically and traditionally, enzymes have been discovered and isolated from pure cultures of microorganisms. The process of obtaining a pure culture of a microorganism is very time consuming, if at all possible. A microorganism of course needs to be known to produce the product or enzyme of interest, preferably at the conditions of interest. This microorganism then needs to be purified from all the other microorganisms in its habitat by differential and selective media in hope to get the microorganism in a pure culture. However, recent findings by metagenomics, where the whole microbial community is considered to represent a meta-organism, have made it clear that the interactions and co-operations between populations of microorganism in a microbial community are so vital that only a fraction (1-10%) of all microorganisms can be obtained in pure cultures. Consequently, the enzymes that have been found so far and are in use in industrial applications today are very much biased towards gene products of the very few microorganisms that can be obtained in pure cultures. Thus, there are some 90-99% of the microorganisms that are not accessible for screening for valuable enzymes with methods that rely on pure cultures of microorganisms[3].

In view of the limitations of pure culturing described above, other methods to enable screening for novel enzymes in full microbial communities are desirable. One way of doing this is to take the route via DNA, using metagenomics and produce a meta-genomic library of microbial communities in natural habitats[4]. However, one drawback of this approach is that all genes need to be cloned, even those that might not be of interest for industrial biotechnology, such as genes coding for e.g. structural proteins. Another drawback of this approach is that the huge number of clones that are produced, all carrying different gene segments, have to be expressed and submitted to either sequence or activity based screening for identification of the correct enzyme.

Recent progress in proteomics, i.e. the large-scale study of proteins expressed by an organism, has also lead to the development of metaproteomics, i.e. the large-scale characterization of the entire protein complement of environmental microbiota at a given point in time[5]. However, up till now metaproteomics has only been used to collect intracellular proteins in order to understand metabolic pathways and interactions among the populations that makes up a certain microbial community[6-8]. Even if it would be desirable to screen for secreted proteins/enzymes in environmental samples this would not be possible since the sample would be too contaminated with interfering substances and the enzymes would be too diluted. For the purpose of screening for secreted proteins (known as secretomics) by microorganisms, so far only microorganisms in pure cultures have been used, often with the aim of finding virulence factors for pathogenic microorganisms[9, 10].

The growing worldwide interest to increase the production of biogas from organic residues, to be used as an alternative fuel, can serve as an important example of an industrial process that clearly would benefit from employing hydrolytic enzymes. However, this will only be possible if enzymes that are effective and have a long lifetime in the prevailing conditions of an anaerobic digester can be found. Much of the organic matter used as substrate in biogas production has a low biological availability, due to being physically and chemically stable, which results in that some substrates display a low degree of degradation. Most suggested pretreatment methods for increasing biogas production rely on energy intensive thermal and/or physical disintegration of various cell walls, with the intention to release the content of the cells. Examples are steam explosion, ultrasonication, electroporation, bead-milling etc. However, even if successful and economically viable, these methods alone will only marginally influence the rate and degree of degradation of the actual cell walls and other structural components that make up a significant part of most organic material.

Figure 1:
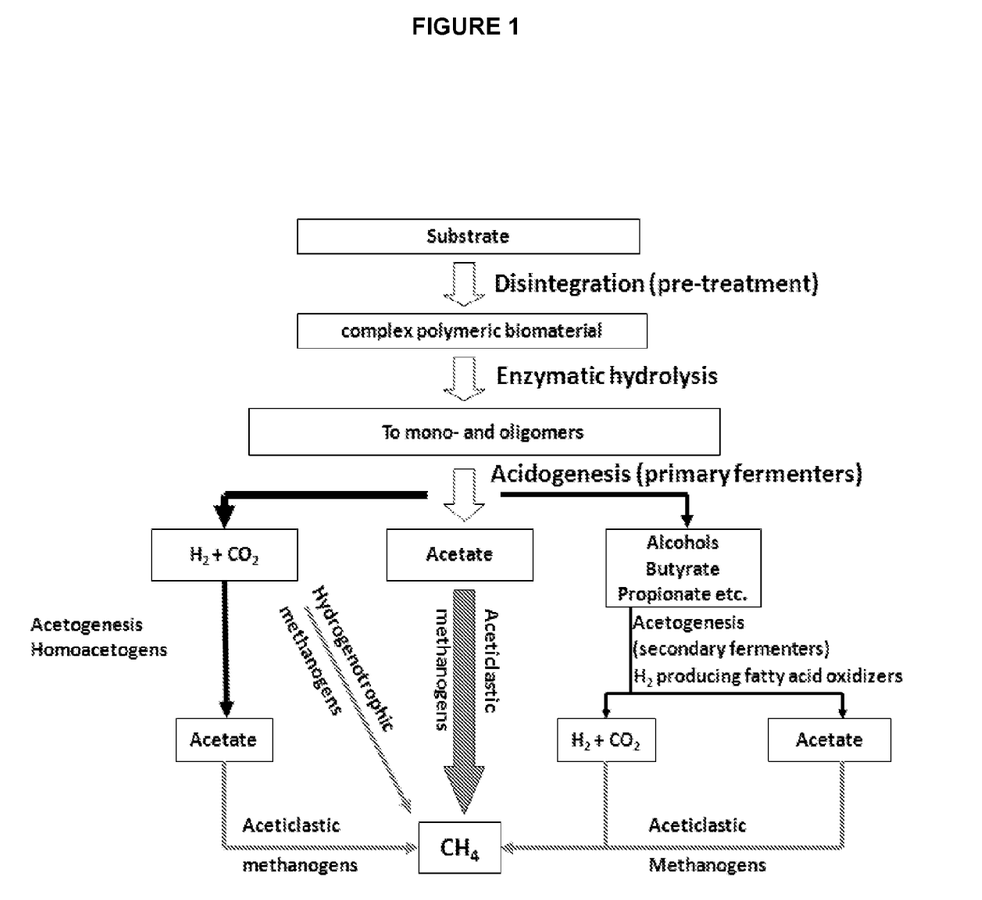
FIG. 1 is a schematic outline of the major steps of anaerobic digestion and biogas production, including main organisms and metabolites.

Although established in many other industrial biotechnological applications, the addition of hydrolytic enzymes in order to increase both the rate and yield of digestion in the biogas production is fairly new. The use of enzymes for this purpose is applicable in processes where the first and second step in methanogenesis, i.e. disintegration and hydrolysis, are rate limiting (see FIG. 1). The idea is that enzymes with specific activity towards various biopolymers such as proteins and polysaccharides will hydrolyze the organic matter and that the addition of hydrolytic enzymes to the process leads to a more effective use of substrates that are difficult to degrade, and to the possible use of various new substrates. Experiments have been made by adding various commercially available hydrolytic enzymes to anaerobic digesters. However, these enzymes have originated from various microorganisms that are not part of microbial communities in methanogenic habitats. Thus, those enzymes are not evolutionarily adapted to the prevailing conditions in an anaerobic digester and the intended use. Consequently, experiments made so far have generally not shown any high success rate.

However, what is clear is that upon addition of recalcitrant organic material, such as cellulose, to an anaerobic digester there is an increase in gas production although this process is very slow. Thus, within the microbial community there are microorganisms present that are able to synthesize and secrete enzymes that are active against e.g. cellulose at the prevailing conditions, but in too small amounts. Such an enzyme or enzymes are of course of a considerable value in increasing biogas production if it would be possible to identify, produce and add them to anaerobic digesters.

SUMMARY OF THE INVENTION

The aim of the present invention is therefore to solve the problems and disadvantages described above by providing a method that is useful for both inducing and identifying enzymes of choice that are optimally adapted to the conditions and substrates of choice, whilst at the same time being independent of pure culturing.

This is achieved according to the present invention by means of a method for rational mining for induced enzyme/enzymes in microbial communities, comprising the steps of:
(a) providing at least one community of microorganisms,
(b) cultivating the microbial populations of said at least one community in at least one container under conditions of choice, where the microorganisms are given a defined culturing medium to eliminate matter deriving from the natural habitat and to allow the microbial community to reach a metabolic steady-state,
(c) removal from at least one container of step (b) of at least one fraction of microorganisms, and transfer of said at least one fraction into at least two separate containers,
(d) providing at least one of the fractions of microorganisms from step (c) with a defined medium which includes an inducing substance and/or a substance against which enzyme/enzymes is/are desired, to induce a regulation of expression of the desired enzyme/enzymes, and at least one of the other fraction(-s) from step (c) with a defined medium without said inducing substance and without said substance against which enzyme/enzymes is/are desired for the purpose of comparison, and maintaining and/or cultivating the fractions of microorganisms, and
(e) withdrawing and analyzing samples of at least one induced fraction and at least one non-induced fraction of step (d) for identification of the induced enzyme/enzymes.

According to one embodiment the container of step (b) is a chemostat or an anaerobic digester.

According to a further embodiment the microbial community originates from animals, plants, insects, soil or aqueous environments.

In one embodiment the defined medium is a medium comprising decomposed organic material, fermentation products and other essential substances, such as salts, vitamins, metals and trace elements.

In another embodiment of the present invention the contents of the samples taken in step (e) are separated into fractions before analyses and identification.

In one embodiment the samples taken in step (e) are subject to purification.

In a further embodiment the samples taken in step (e) are subject to concentration.

In a further embodiment the purification and/or concentration is done by separation methods based on the varying physicochemical properties of proteins.

In another embodiment the analyses and identification of step (e) is done by 1 or 2 dimensional gel electrophoresis or chromatography followed by comparison of the results for the two fractions.

The aim of the present invention is further achieved by means of a method for rational mining for induced enzyme/enzymes and production thereof, comprising the steps of:
 (a) providing at least one community of microorganisms,
 (b) cultivating the microbial populations of said at least one community in at least one container under conditions of choice, where the microorganisms are given a defined culturing medium to eliminate matter deriving from the natural habitat and to allow the microbial community to reach a metabolic steady-state,
 (c) removal from at least one container of step (b) of at least one fraction of microorganisms, and transfer of said at least one fraction into at least two separate containers,
 (d) providing at least one of the fractions of microorganisms from step (c) with a defined medium which includes an inducing substance and/or a substance against which enzyme/enzymes is/are desired, to induce a regulation of expression of the desired enzyme/enzymes, and at least one of the other fraction(-s) from step (c) with a defined medium without said inducing substance and without said substance against which enzyme/enzymes is/are desired for the purpose of comparison, and maintaining and/or cultivating the fractions of microorganisms,
 (e) withdrawing and analyzing samples of at least one induced fraction and one non-induced fraction of step (d) for identification of the induced enzyme/enzymes,
 (f) analyzing the identified enzyme/enzymes, deriving the DNA sequence/sequences that codes for the enzyme/enzymes, and
 (g) producing the identified enzyme/enzymes by use of a host organism or the original parental organism.

According to one embodiment the container of step (b) is a chemostat or an anaerobic digester.

According to a further embodiment the microbial community originates from animals, plants, insects, soil or aqueous environments.

In one embodiment the defined medium is a medium comprising decomposed organic material, fermentation products and other essential substances, such as salts, vitamins, metals and trace elements.

In another embodiment of the present invention the contents of the samples taken in step (e) are separated into fractions before analyses and identification.

In one embodiment the samples taken in step (e) are subject to purification.

In a further embodiment the samples taken in step (e) are subject to concentration.

In a further embodiment the purification and/or concentration is done by separation methods based on the varying physicochemical properties of proteins.

In another embodiment the analyses and identification of step (e) is done by 1 or 2 dimensional gel electrophoresis or chromatography followed by comparison of the results for the two fractions.

In another embodiment the enzyme/enzymes that is/are identified is/are analyzed and classified by e.g. mass spectrometry and de-novo sequencing.

The aim of the present invention is further achieved by means of a method for rational mining for induced enzyme/enzymes, comprising the steps of:
 (a) providing a community of microorganisms,
 (b) cultivating the microbial populations of the community in a container under conditions that mimic the conditions of the microbial community's natural habitat, where the microorganisms are given a defined culturing medium to eliminate matter deriving from the natural habitat and to allow the microbial community to reach a metabolic steady-state,
 (c) removal from the container of step (b) of two fractions of microorganisms, and transfer of said two fractions into two separate containers,
 (d) providing one of the fractions of microorganisms from step (c) with a defined medium which includes a substance against which enzyme/enzymes is/are desired, to induce a regulation of expression of the desired enzyme/enzymes, and the other fraction from step (c) with a defined medium without said substance for the purpose of comparison, and maintaining and/or cultivating the two fractions of microorganisms, and
 (e) withdrawing and analyzing samples of the two fractions of step (d) for identification of the induced enzyme/enzymes.

According to one embodiment the container of step (b) is a chemostat or an anaerobic digester.

According to a further embodiment the microbial community originates from animals, plants, insects, soil or aqueous environments.

In one embodiment the defined medium is a medium comprising decomposed organic material, fermentation products and other essential substances, such as salts, vitamins, metals and trace elements.

In another embodiment of the present invention the contents of the samples taken in step (e) are separated into fractions before analyses and identification.

In one embodiment the samples taken in step (e) are subject to purification.

In a further embodiment the samples taken in step (e) are subject to concentration.

In a further embodiment the purification and/or concentration is done by separation methods based on the varying physicochemical properties of proteins.

In another embodiment the analyses and identification of step (e) is done by 1 or 2 dimensional gel electrophoresis or chromatography followed by comparison of the results for the two fractions.

The aim of the present invention is further achieved by means of a method for rational mining for induced enzyme/enzymes and production thereof, comprising the steps of:
 (a) providing a community of microorganisms,
 (b) cultivating the microbial populations of the community in a container under conditions that mimic the conditions of the microbial community's natural habitat, where the microorganisms are given a defined culturing medium to eliminate matter deriving from the natural habitat and to allow the microbial community to reach a metabolic steady-state, (c) removal from the container of step (b) of two fractions of microorganisms, and transfer of said two fractions into two separate containers, (d) providing one of the fractions of microorganisms from step (c) with a defined medium which includes a substance against which enzyme/enzymes is/are desired, to induce a regulation of expression of the desired enzyme/enzymes, and the other fraction from step (c) with a defined medium without said substance for the purpose of comparison, and maintaining and/or cultivating the two fractions of microorganisms, and (e) withdrawing and analyzing samples of the two fractions of step (d) for identification of the induced enzyme/enzymes.

(f) analyzing the identified enzyme/enzymes, deriving the DNA sequence/sequences that codes for the enzyme/enzymes, and (g) producing the identified enzyme/enzymes by use of a host organism or the original parental organism.

According to one embodiment the container of step (b) is a chemostat or an anaerobic digester.

According to a further embodiment the microbial community originates from animals, plants, insects, soil or aqueous environments.

In one embodiment the defined medium is a medium comprising decomposed organic material, fermentation products and other essential substances, such as salts, vitamins, metals and trace elements.

In another embodiment of the present invention the content of the samples taken in step (e) are separated into fractions before analyses and identification.

In one embodiment the samples taken in step (e) are subject to purification.

In a further embodiment the samples taken in step (e) are subject to concentration.

In a further embodiment the purification and/or concentration is done by separation methods based on the varying physicochemical properties of proteins.

In another embodiment the analyses and identification of step (e) is done by 1 or 2 dimensional gel electrophoresis or chromatography followed by comparison of the results for the two fractions.

In a further embodiment the enzyme/enzymes that is/are identified is/are analyzed and classified by e.g. mass spectrometry and de-novo sequencing.

The present invention also relates to enzymes that are produced using the methods as described above.

BRIEF DESCRIPTION OF THE DRAWINGS

The present invention will be further described with reference to the enclosed drawings.

DETAILED DESCRIPTION OF PREFERRED EMBODIMENTS OF THE INVENTION

Definitions

"Defined medium" refers to a chemically defined medium for culture growth wherein those nutrients and other components required for growth of the microbial community are supplied. Compounds which the organisms themselves are capable of synthesizing using their own metabolic pathways are generally not included in the medium. The defined medium also contains components that adjust the properties of the medium to mimic the conditions prevailing in the natural habitat of the microbial community. As a result, the content of a particular defined medium depends on the nutritional needs and conditions of the natural habitat of the microbial community of interest. Standard literature references describing the needs of the microbial community can be consulted for finding the composition of the correctly defined medium for various microbial communities.

"Conditions" mean the physical and chemical state of the environment in which the microbial community exists. Examples of different conditions relate to e.g. temperature, pH, water availability, oxygen levels and ionic strength.

"Conditions of choice" means conditions chosen and adapted for the mining for desired enzyme/enzymes with specific characteristics.

"Chemostat" means a device for continuous culturing of microorganisms.

"Induce enzyme" means to affect the regulation of enzyme expression, both upwards and downwards.

"Inducing substance" means a substance that is added to the microbial community with the aim to affect the regulation of enzyme expression.

"Metabolic steady-state" means a stable condition of metabolic activity that does not change over time.

"Nullified reactor" means a chemostat in which the microbial community has been kept under constant conditions, supplied with a defined medium, so that residuals from the natural habitat has been washed out and/or consumed and the microbial community has reached a metabolic steady-state in an environment of known composition.

"Anaerobic digester" means an artificial biodegradation facility for the anaerobic digestion of organic substrate to produce biogas.

"Batch culture" means a closed-system microbial culture.

"Meta-proteomics" is the study of all protein samples recovered directly from environmental samples. Metaproteomics should be used to classify experiments that deal with all the proteins identified from complex communities, where individuals cannot be binned into species or organism types.

"Secretomics" relates to the subset of the proteome consisting of proteins actively exported from a cell type.

"Meta-secretomics" is the study of samples of all the actively exported proteins from complex microbial communities, where individuals cannot be binned into species or organism types.

The method according to the present invention is not limited to the use of enzymes that catalyze any specific pathway. The method is general and can be used to induce and identify any industrially important enzyme from e.g. a biogas process, a hot spring or any other microbial habitat whose environment can be cleaned whilst keeping the microbial community viable using a defined medium, regardless if it is an enzyme that affects different types of fats, proteins, polysaccharides or any other organic molecules.

The population of microorganisms according to the present invention can e.g. originate from animals, insects, plants, soil, aqueous environments, extreme environments with high or low oxygen content, high or low pH, high or low temperature, high pressure or high salt concentration. The populations of microorganisms may further originate from methanogenic habitats such as an anaerobic digester, the rumen of ruminants, hindgut of cellulolytic insects, anoxic sediments or cecum of cecal animals.

The enzyme/enzymes that are identified and/or produced according to the present invention are preferably suitable for applications in industrial and environmental biotechnology, production of renewable energy from biobased feedstocks, production of biogas, production of bioethanol, food/feed industry, dairy industry, baking industry, wine and fruit juice industry, brewing industry, textile industry, leather industry, applications in detergents, pulp and paper industry, processing of fats and oils, application as digestive aid, chemical synthesis and for degradation of harmful compounds at contaminated sites or at waste water treatment plants, but may of course be suitable for many other types of applications.

The present invention can be envisaged to be used to find enzymes for numerous of other applications, which is limited only by imagination. For example, one possible use of the present invention is to use a bacterial population taken from a waste water treatment plant to find and produce enzymes that decompose residues of medicaments in waste water. This is a very important aspect, since these residues can be very detrimental to both humans and animals, e.g. making fish sterile and affecting human fetus.

Another example is for finding enzymes for the production of biogas in anaerobic digesters, in which the microbial populations of the community work together to break down organic matter by anaerobic digestion. If it was possible to find enzymes from within the microbial community of methanogenic habitats, as with the present invention, and then produce and add these enzymes to anaerobic digesters, this could very well prove to be a successful route.

The microbial process of anaerobic digestion of organic material to carbon dioxide and methane (i.e. biogas) is also an important example of the practicability of the present invention as this is possibly one of the most difficult processes to work with. The microbial community is made up of several populations with very different generation times ranging from 1-2 days for primary fermentative bacteria to more than a week for some methanogenic archaea. Further, the microbial community is made up of primary fermentative, secondary fermentative, homoacetogenic, sulfate reducing and hydrogen producing fatty acid oxidizing bacteria in addition to hydrogenotrophic and aceticlastic archaea. Thus, the microbial community in anaerobic digesters represents a highly complex, cooperative and syntrophic community and there will therefore be present a high number of metabolites in the medium from which enzymes need to be purified (see FIG. 1 for a schematic outline of the process of anaerobic digestion, including main organisms and metabolites). It is further an anoxic process supporting the life of methanogenic archaea, of which some are the most oxygen sensitive organisms on earth.

However, although one of the most difficult microbial communities to work with, the many steps involved in methanogenesis are a good indication of the feasibility of the present invention. Thus, if for some reason the defined medium or the conditions are not able to support life for one or more of the populations there will be an imbalance in the microbial population which will lead to accumulation of metabolites and/or that the process will not lead all the way to methane. On the other hand, if the process leads all the way to methane production this is in itself proofs that all the necessary populations are viable and that the full microbial community is screened for induced and expressed enzymes at the desired condition.

A method that enables a rational way of inducing, finding and identifying enzymes for diverse areas is enzyme mining in microbial communities according to the present invention.

Figure 2:
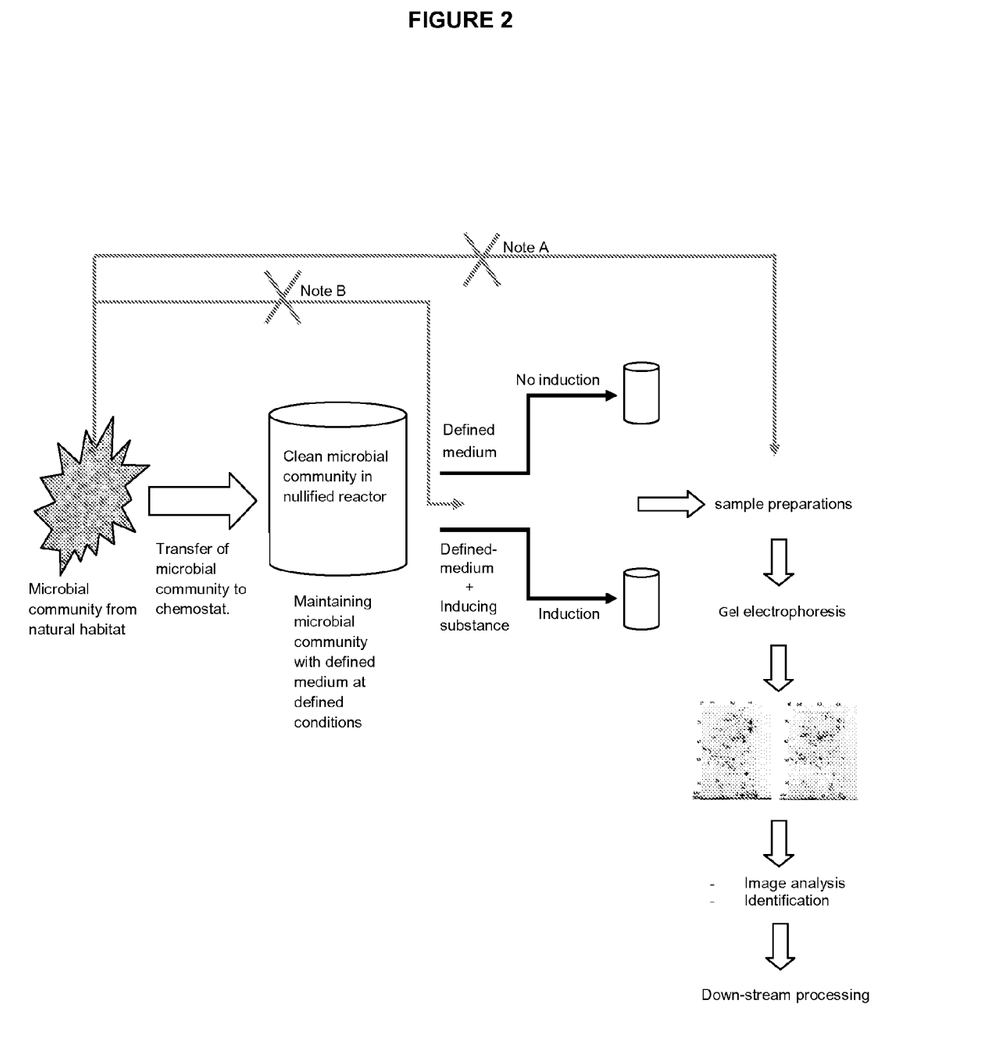
FIG. 2 is a schematic view of a method according to the present invention where the microbial community, that originates from a habitat of choice (e.g. an anaerobic digester), is cultured in a chemostat with a defined medium and under defined conditions to obtain a nullified reactor.

In one example of the present invention a microbial community is taken from an anaerobic digester, as can bee seen in FIG. 2. According to another example, the microbial community can be taken from any other microbial habitat. The microbial population is then transferred to a chemostat, operated to mimic the natural habitat of the microbial community or, alternatively, operated under conditions of choice, where the microorganisms are fed with a nutrition solution of known composition, i.e. a chemically defined medium. The composition of the defined medium and/or conditions that is/are used depends on the natural habitat of the microbial community and/or on desired enzymes and/or enzyme characteristics. By cultivation of the microbial community with a defined medium the content of the chemostat becomes clean, since particulate matter and other contaminants of the natural habitat no longer will be present and the populations of the microbial community are kept alive and viable. This results in that a nullified reactor at steady-state is established, which does not have any memory of the original substrate comprising a lot of particulate matter and other contaminants. Furthermore, the microorganisms of the nullified reactor do not have to express large amounts of hydrolytic enzymes to obtain amino acids, sugars etc that are needed, since they are fed with decomposed substrates, which results in a steady-state expression of enzymes.

The nullified reactor according to the present invention is very important for a multitude of reasons. To search for enzymes produced by microbial communities in natural habitats without induction would not be rational since even if it was possible to purify and obtain the enzymes in high enough concentration their function would still be unknown. Thus cloning and screening for sequence or activity for all proteins would still be necessary, i.e. it is a non-rational, non-feasible route (see A in FIG. 2). There would further be no point in trying to induce regulation of an enzyme directly in the original habitat of a microbial community, since it is too contaminated and complex, and the concentration of microorganisms and enzymes is too low. Thus, fractionation, purification and concentration of the enzymes or the microorganisms of interest are thereby almost impossible, i.e. it is a non-feasible route (see B in FIG. 2). Moreover, it would be very difficult to identify the induced enzymes of choice in samples collected directly from the natural habitat since there is an already ongoing and fluctuating active production of various enzymes by the microbial community.

From the clean microbial community of the nullified reactor two fractions are taken and the cells are preferably concentrated by for example centrifugation and washed with a defined medium once or several times and thereafter transferred into two separate containers for batch culturing. Alternatively, at least one fraction can be taken, followed by transfer of the at least one fraction into two separate containers.

Examples of suitable containers for batch culturing are flasks, bottles or any type of vessel. However, the cultivation of these two fractions can be done either in a chemostat or in batch cultures. The purpose of the batch culturing is not necessarily to culture the microorganisms to a higher cell density, as in the regular use of batch cultures, but to find what enzymes are produced by the microbial community in response to a certain substance. The regular way to grow microbial cells in a batch culture normally encompasses inoculation of a small volume of pure culture into a larger volume of medium (normally at an approximate 1:100 ratio). Contrary to batch cultures of pure cultured microorganisms, a batch experiment with the normally small inoculum would however not work for rational enzyme mining since, according to the present invention, a microbial community is maintained in the nullified reactor. In a microbial community different populations of microorganisms have different generation times, which can range from hours to even weeks. Thus, if a small inoculum was used, different growth rates in the batch culture would lead to a microbial imbalance. Therefore it is necessary to sample a larger volume of microorganisms from the nullified reactor, which is concentrated by centrifugation, so what is added to the batch cultures is a complete microbial community that is already from the start in balance.

Thus, importantly, the nullified continuous reactor serves several purposes that are instrumental for the present invention of rational enzyme mining from microbial communities as (i) it provides a "clean" starting material that has no "memory" of the original substrate (ii) it provides a microbial community that is at steady-state and viable under the chosen conditions and thus have the ability to produce enzymes that are active and stable under the said conditions (iii) it provides a microbial community that is in balance in such a way that each type of microorganism is present in a correct number relative to other microorganisms so that the microbial community is able to metabolize all parts of the substrate or the produced metabolites at the same rate and (iv) it provides a starting material with a high absolute number of each and all microorganisms so that there is a high probability that any expressed protein/enzyme that is present after induction is present in such large amount that it can be detected.

One of the fractions of the microbial community is provided with a defined medium, including an inducing substance and/or a substance against which one or more enzymes are desired. This will disturb the steady-state and at some point result in a response in enzyme expression regulation. The other fraction is provided only with a defined medium, i.e. the medium does not comprise an inducing substance or a substance against which one or more enzymes are desired. The reason to this arrangement is that the content of the container that is given only the defined medium is used for comparison to be able to identify the enzyme/enzymes that have been induced in the other container, i.e. the content of the container given only defined medium is used as a reference showing what proteins/enzymes that are present naturally in the microbial community at steady-state.

The addition of exactly the substance or substances against which enzyme/enzymes are desired results in that only the microorganisms that are able to produce these enzyme/enzymes will react. Thus, contrary to e.g. metagenomics, where the DNA of the full microbial community is cloned and screened, according to the present invention the addition of a target substance results in that the microbial community reacts and regulates the expression of the requested enzyme/enzymes. Thus, by adding a single known substance to a microbial community, viable under certain conditions, several goals are achieved since (i) the activity of the identified enzyme is known, for example if adding cellulose this will induce the regulation of expression of cellulases or if adding keratin this will induce the regulation of expression of keratinases, and (ii) the expressed and identified enzyme will be stable under the conditions that the microbial community was selected for and no further screening is necessary.

After leaving the induced microbial population to express enzymes, while maintaining and or cultivating the fractions of microorganisms, samples are taken from the container with the induced population and also from the other container used as a reference. At this point the samples can be fractionated to find different proteins/enzymes in different fractions for example (i) the liquid phase could be collected to identify free extra-cellular proteins/enzymes (ii) the substrate could be collected to search for substrate adsorbed proteins/enzymes (iii) the microorganisms could be collected to identify cell-bound extracellular proteins/enzymes or (iv) the microorganisms could be collected to identify intracellular proteins/enzymes. The proteins/enzymes that are collected are then purified and concentrated. Since, the samples are taken from a rather clean environment of known composition, due to the cultivation in a chemically defined medium, fractionation, purification and concentration of the proteins/enzymes can be done with a number of established techniques based on the physicochemical properties of proteins, such as centrifugation, ultra filtration, dialysis, electrophoresis, iso-electric focusing, specific precipitation etc.

After purification of the protein/enzyme samples they are analyzed by e.g. gel electrophoresis or chromatography. The purified samples, when using gel electrophoresis, are separated on the gels with regard to size or, alternatively, size combined with charge. One gel is used for the sample that has been induced and one gel for the reference sample, or, alternatively, the samples are run on the same gel. These gels will give patterns reflecting the enzyme expression from the microbial community at steady-state that has not been induced with any substance and also the enzyme expression from the induced sample. By analysis and comparison of the gel/gels, e.g. by overlapping, it is possible to identify protein spots that differ between the gel from the induced sample from the gel with the reference sample. These spots represent potential enzymes with activity of choice that have been rationally induced using a substance of interest and identified from the microbial community, viable under predetermined conditions, according to the present invention.

After this comparison, interesting enzyme spots may be cut out from the gels and analyzed with established methods, such as mass-spectrometry and de-novo sequencing in order to classify the enzyme, find the likely function of the enzyme, what the amino acid sequence of the enzyme is, etc.

Using the information from this analysis it is possible to derive the DNA sequence and to clone or construct the gene in order to produce the enzyme for further tests regarding activity, stability, pH- and temperature optimum etc. It is further possible to use the DNA sequence for production of the enzyme/enzymes in a host organism or the original organism on an industrial scale, e.g. for use in any of the earlier described processes.

Thus, by using the method according to the present invention it is not only possible to find and produce new enzymes with properties superior to those of already known enzymes but also to identify new unique enzymes never used industrially by man since the whole microbial population is used as a source.

Examples

The following examples illustrate only preferred embodiments of the present invention. The examples are only illustrative and should not be construed as limiting the invention in any way. The examples further describe how the present invention enables rational enzyme mining of enzymes secreted into the medium, which is the most complex problem to solve.

Nullified Reactor

The anaerobic microbial community was collected in the form of a digestate from a full-scale anaerobic digester treating slaughter house and food waste. The digestate was transferred under oxygen exclusion to a chemostat operated under anaerobic conditions as an anaerobic digester with a total volume of 15 liters and an active volume of 9 liters. The reactor was during a start up phase fed with the same substrate as the full-scale digester and run under mesophilic conditions (38° C.) with an average retention time of 35 days and an organic loading rate (OLR) of 2.5 g volatile solids (VS)/L and day. During the experiment several parameters were monitored in order to verify that the bacterial population was stable and at steady state, including: digestate total dry solids (DS) and volatile solids (VS), volatile fatty acids (VFA), nitrogen, pH and alkalinity. Gas production and methane content were measured online with a milli gas counter (MGC-10, Ritter, Germany) and an IR gas sensor (Bluesense Gas sensor GmbH, Germany) and through gas sampling. VFA was measured with a GC-FID (Glarus 500, Perkin-Elmer), column: Perkin Elmer Elite-FFAP (Perkin-Elmer, USA). Ammonium-nitrogen was analyzed according to FOSS Tecators application sub note 3502 with a Kjeltec 8200 (FOSS in Scandinavia, Sweden). The total organic nitrogen, Kjeldhal-nitrogen, was analyzed according to Tecators AN 300 Sv 1999-04-09 v. 2 with a Kjeltec 8200 (FOSS in Scandinavia, Sweden). pH was measured according to Swedish standard EN 12176 with the pH electrode WTW Inolab pH Level 2 (Weilheim, Germany). Alkalinity was measured with a hydrochloride acid titration method according to guidelines in Swedish standard EN ISO9963. Total solids and volatile solids were analyzed according to Swedish Standard SS 028113.

When all monitored parameters were stable the substrate was replaced with a defined medium designed to provide all nutritional components and conditions that are required by the anaerobic microbial community. The medium was designed based on several anaerobic media used for growth of methanogenic communities[11-15] and consisted of the following:

Buffer and minerals: 10 mM $KH_2PO_4$, 10 mM $Na_2HPO_4$, 61 mM $NaHCO_3$, 5.6 mM $NH_4Cl$, 3.5 mM $Na_2SO_4$, 0.5 mM $MgCl_2.6H_2O$, 0.3 mM $FeCl_2.4H_2O$, Vitamins: 1 µM pyridoxamine-2HCl (Vit. $B_6$), 0.81 µM nicotinic acid (Vit, $B_3$), 0.57 µM L-ascorbic acid (Vit. C), 0.36 µM p-aminobenzoic acid, 0.24 µM lipoic acid, 0.22 µM thiamin hydrochloride (Vit. $B_1$), 0.13 µM riboflavin (Vit. $B_2$), 0.11 µM calcium D(+) pantothenate (Vit. $B_5$), 0.08 µM biotin (Vit. $B_8$), 0.05 µM folic acid (Vit. $B_9$), 0.04 µM vitamin $B_{12}$, Trace elements: 0.65 µM $H_3BO_3$, 0.37 µM $AlCl_3$, 0.29 µM $ZnCl_2$, 0.21 µM $CoCl_2.6H_2O$, 0.18 µM $CuCl_2.2H_2O$, 0.15 µM $MnCl_2.2H_2O$, 0.105 µM $NiCl_2.6H_2O$, 0.06 µM $Na_2SeO_3.5H_2O$, 0.06 µM $Na_2WO_4.5H_2O$, 0.04 µM $(NH_4)_6Mo_7O_{24}.4H_2O$, Carbon and nitrogen sources: 170 mM glucose, 170 mM amino acids (acid hydrolyzed casein), 22 mM saccharose and 22 mM Ca-lactate, Fermentation products: 15 mM ethanol, 15 mM methanol, 9 mM acetic acid, 3 mM propionic acid, 1.5 mM butyric acid and 1.5 mM formic acid.

Depending on process stability as evaluated by VFA concentration the OLR of the defined media was between 0 and 2 g VS/L and day.

Batch Induction

A sample of 200 mL of digestate was collected from the chemostat 19 months (see arrow in FIG. 3A-D) after the switch to the defined medium. The sample was split into two aliquots of 100 mL and transferred to two centrifuge tubes which were thereafter centrifuged at 250 g for 5 minutes to allow for any particulate matter to sediment. The remaining supernatant was then centrifuged at 9000 g for 20 min. The supernatant was poured off and the pellet was re-dissolved in a de-gassed washing buffer consisting of the defined medium minus the carbon source and fermentation products. The samples were once again centrifuged and the supernatant was poured off. The bacterial cell pellet was thereafter used to start new bacterial population cultures in batch flasks (544 ml flasks with rubber septum). Both flasks contained 250 mL of the defined medium described above but with an organic loading of 0.75 g VS/L. One of the flasks was also supplemented with the new, polymeric, carbon source cellulose in the form of Whatman paper (nr 597) to an additional organic load of 0.75 g VS/L. Gas production was determined by pressure measurements (Testo 312-3, Germany) and methane content was measured in withdrawn gas-samples by GC-FID (Glarus 500, Perkin-Elmer), column: packed Porapak T 80/100 Mesh (Perkin-Elmer, USA).

2-Dimensional Electrophoresis (2-DE). Sample Preparation and Gels Sampling for 2-DE After 4 days 80 ml of sample from each batch culture was transferred to 2×50 ml centrifugation tubes (Sarstedt). The samples were centrifuged for 45 min at 9 000 g at 4° C. in a Hettich R35 centrifuge. The supernatant was collected for sampling of free extra-cellular proteins/enzymes and the pellets were discarded. The samples were frozen in liquid nitrogen and freeze-dried for two days to reduce the sample volume to approximately 4 ml.

Protein Precipitation

The proteins were precipitated using a 20% trichloroacetic acid (TCA)/acetone mixture (Sigma-Aldrich) containing 0.2% dithiothreitol (DTT). The samples of 4 ml were mixed with 20 ml precipitation solution and the proteins were precipitated overnight at −20° C. and thereafter pelleted by centrifugation at 9 000 g for 45 min at −15° C. The pellets were washed twice with 2 ml of acetone at −20° C. Subsequently the pellets were resuspended and allowed to stand in 2 ml acetone for 1 h at −20° C. The acetone was removed after an additional centrifugation and the white pellets were allowed to air-dry for 10 min.

Gel Filtration and Sample Concentration

The protein pellets were dissolved in 2 ml of 8 M urea and each sample was applied to a PD-10 desalting coulomn (GE-Healthcare) equilibrated with 8 M urea. The samples were eluted with 3 ml 8 M urea. The first and last 0.75 ml of liquid was discarded and the middle fraction of 1.5 ml were collected for each sample. The collected fractions were concentrated using an Amicon Ultra-2 ml pre-launch centrifugal filter (Millipore) with a molecular weight cut-off of 10 kDa, reducing the sample volume from 1.5 ml to approximately 100 µl.

Protein Quantification

The protein concentration of the samples was determined with a Nanodrop ND-1000 spectrophotometer (NanoDrop Technologies Inc.) using the Protein A280 method. The protein concentration was calculated by comparison to a bovine serum albumin standard curve in 8 M urea.

2-DE. $1^{st}$ Dimension (Isoelectric Focusing)

An aliquot of sample containing 120 µg protein was diluted to a final volume of 140 µl in lysis buffer (8 M urea, 1% (w/v) CHAPS, 0.4% DTT and 0.5% carrier ampholytes, Bio-Rad). The mixture was allowed to stand for 30 min at room temperature. The samples were centrifuged at 22 000 g for 30 min and the supernatant was loaded via anodic cup loading to a pre-swollen 11 cm IPG strip, pH 4-7 (Bio-Rad). A voltage of 200 V was applied for 6 h to allow the proteins to enter the gel.

The following voltage ramp protocol on the Protean IEF cell (Bio-Rad) was used: 30 min 250 V rapid voltage ramping, 1 h 8000 V slow voltage ramping, rapid voltage ramping to 20 kVh, 50 V rapid ramping for 20 h (holding step). The IPG strips were re-focussed for 15 min at 8000V prior to the $2^{nd}$ dimension analysis.

The IPG strips were equilibrated under gentle agitation for 15 min in equilibration base buffer (6 M urea, 30% (w/v) glycerol, 2% (w/v) SDS in 0.05 M Tris-HCl buffer (pH 8.8)) and 50 mg DTT (Sigma-Aldrich) per strip. Subsequently the strips were equilibrated for 15 min in equilibration base buffer containing 200 mg Iodoacetamide (Bio-Rad) per strip.

2-DE. $2^{nd}$ Dimension (Electrophoresis).

The second dimension was run on the Criterion Cell System (Bio-Rad). Bio-Rad's Criterion 10.5-14% Tris-HCl gels were run in the TGS buffer system at 50 V for 30 min and followed by 200 V for 50 min. 5 µl Fermentas Pageruler plus prestained Protein Ladder was used as molecular weight standard. After electrophoresis the gels were stained with SYPRO ruby fluorescent stain (Invitrogen) according to the manufacturer's protocol.

The gels were scanned and documented with A FLA-5100 imaging system (Fuji-Film) using a SHG blue laser at 473 nm.

Results and Discussion

Nullified Reactor

Except for a short period (approx. 9 months after the switch to the defined medium) when technical problems occurred (leakage to air), the chemostat could be stably operated during the full experiment to reach a nullified reactor.

Figure 3A:
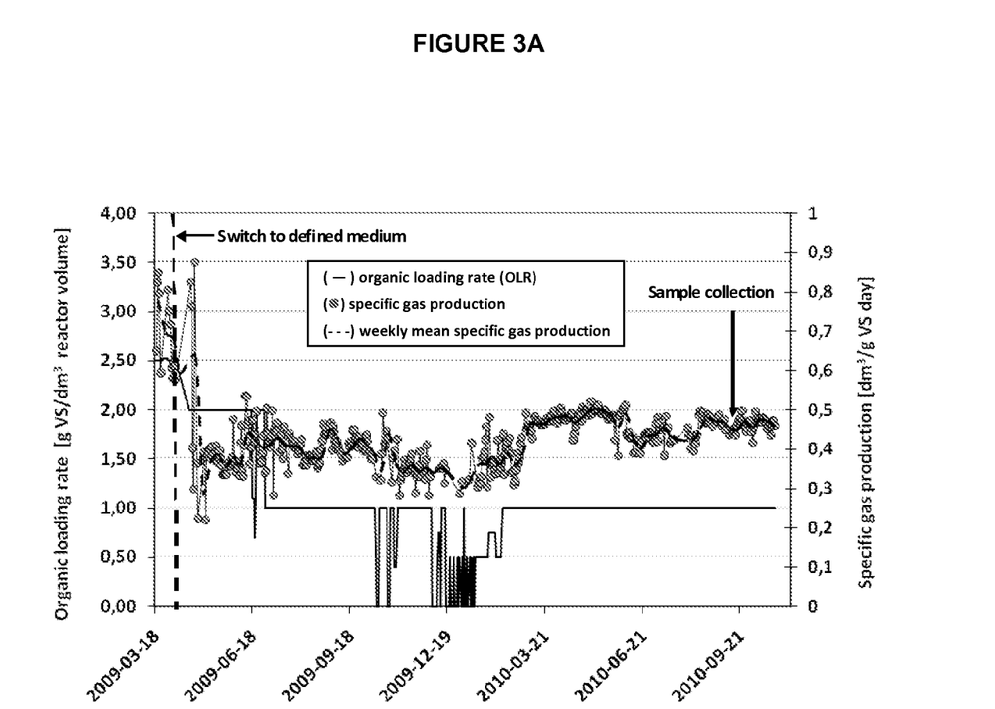
FIG. 3A-3D show registered data and time points for main events (switch from slaughter house waste to defined medium and sample collection for batch cultures) for a chemostat started with a microbial community from an anerobic digester.

Importantly, the bacterial community in the chemostat maintained methane gas production during the full experiment. In FIG. 3A the relationship between organic loading rate and gas production is illustrated. After an appropriate OLR for the defined medium of 1 g VS/L and day was found, the gas production maintained stable (the decrease in organic loading rate midterm of the experiment was a necessary response to the increasing acids during the technical problems). The stable production of biogas is important because it shows that the microbial community is stable in the sence that all types of microorganisms that are necessary to metabolize the carbon sources all the way from monomers via fermentation products to methane are present also after feeding with the defined culturing medium.

Figure 3B:
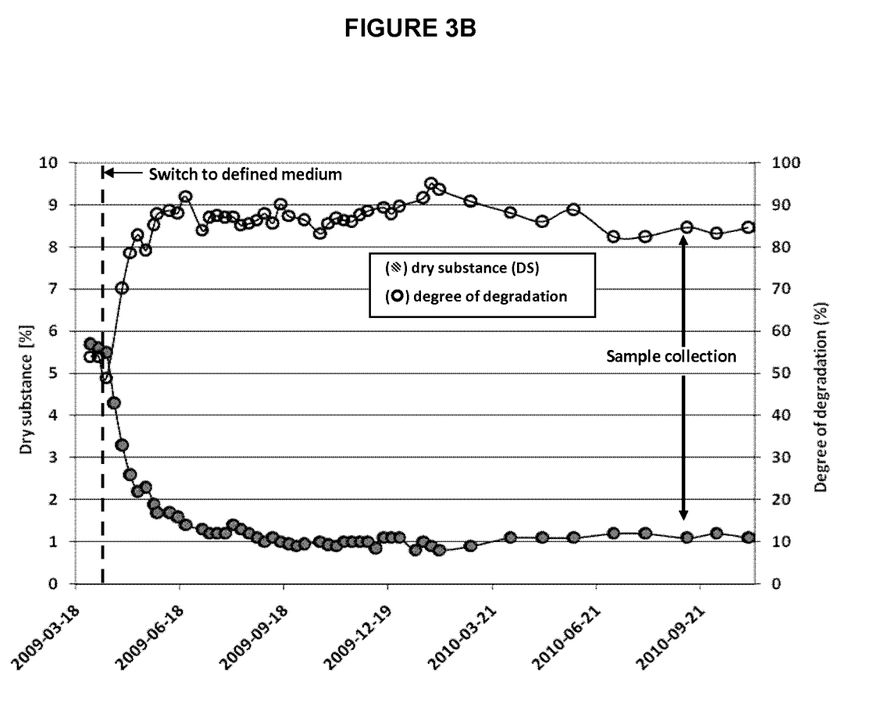

As illustrated in FIG. 3B the total solids dropped from 5.5% to 1% after approximately 5 months after the onset of feeding with defined medium. Thus, the residues of the original substrate in the form of slaughter house waste have been either degraded or washed out depending on whether the material is biologically accessible or not. Arithmetically, 95% of an inert substance would be washed out after 3 retention times (105 days). This is important because once the dry substance (DS) is stable at very low values it shows that there are no residual components from the original substrate left in the reactor. Thus, the remaining volatile solids (VS) of the dry substance (DS) is made up of the bacterial community solely. Furthermore, after the switch in substrate the degree of degradation increased from 55% to 85%. This is expected since the defined medium only contains carbon sources in the form of monomeric sugars and amino acids that are microbially accessible. Thus, more or less all the carbon is converted to gas in the process. It is also interesting to note that this increase of 30% in degree of degradation is what could possibly be reached if all organic material in e.g. slaughter house waste could be hydrolyzed to monomers. A 100% degree of degradation is not possible as some of the carbon is necessary to produce components of new microorganisms.

Figure 3C:
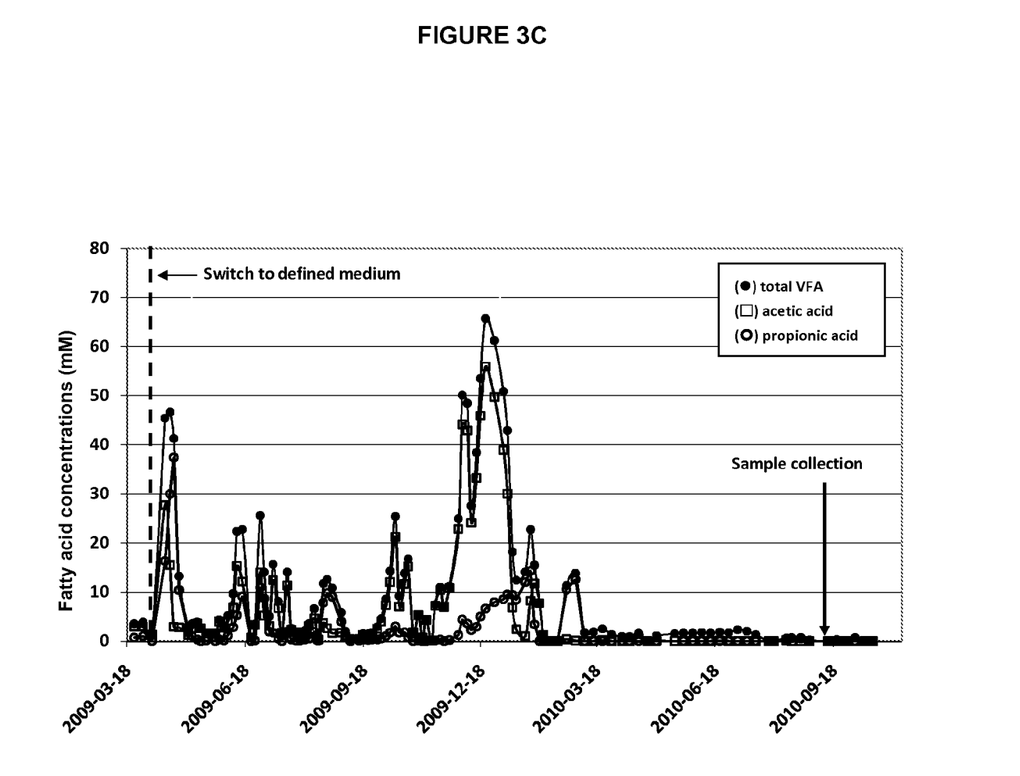

In order to provide substrate for the primary fermentative bacteria the defined medium contained the carbon sources glucose, saccharose and amino acids. This is however not the substrate for secondary fermentative bacteria or methanogens, so in order to satisfy the substrate needs of all the microorganisms the defined medium also comprises low concentrations of fermentation products (alcohols and fatty acids). As is illustrated in FIG. 3C there is a sudden increase in acids at the switch from the original substrate to the defined medium which is due to that acids are both produced by the residual original substrate, the added highly microbially accessible carbon sources and the added fatty acids. However, it also shows that the metabolically downstream microorganisms are able to cope with the increasing VFA content as the concentration falls after a few weeks and is thereafter fairly stable (below 30 mM total VFA) until problems with the chemostat occurred. However, even after the technical problems leading to fatty acid concentrations of above 60 mM, the microbial community could be maintained, and after the technical problem was solved fatty acid concentration remained very low.

Figure 3D:
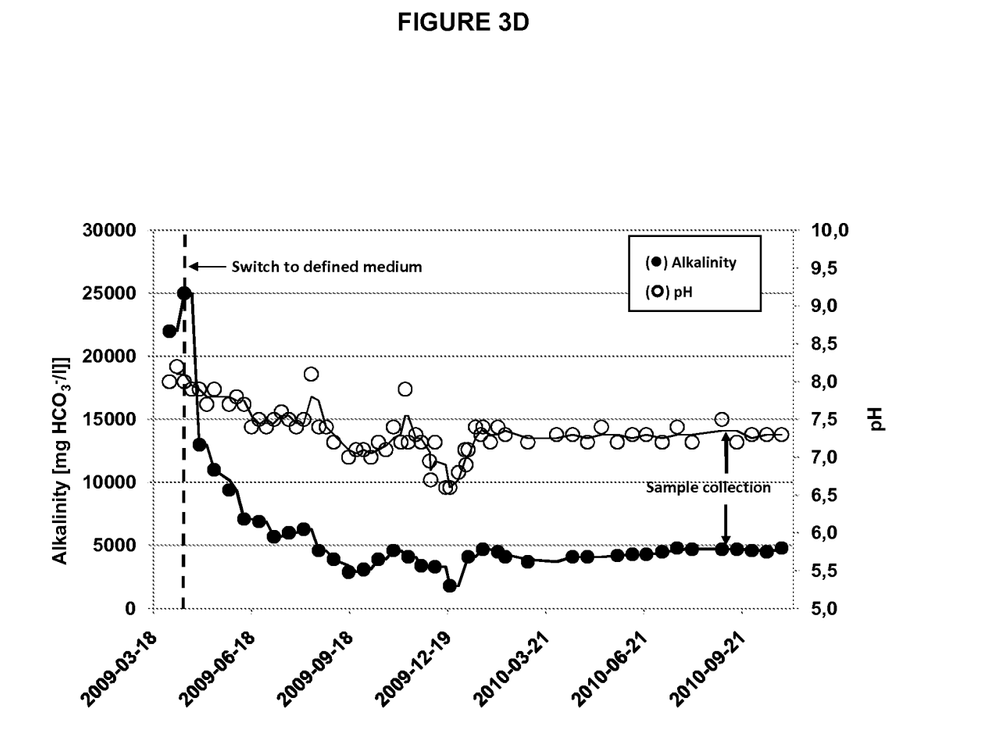

The defined medium has a much lower pH buffering capacity than mixed organic material, e.g. slaughter house waste, and the alkalinity dropped from above 20.000 to approx. 5.000 $HCO_3$ equivalents per liter (FIG. 3D). This is however enough since acidic metabolites are consumed at a high rate by secondary fermenters and methanogens that are viable and active in the reactor. Thus pH dropped only by approximately 0.7 units from the switch from slaughter house waste to defined medium (FIG. 3D).

To conclude it is shown that it is possible to compose and use a defined culturing medium under conditions that maintains the full microbial community that is needed to anaerobically convert a carbon source all the way to carbon dioxide and methane via microorganisms performing primary fermentation, secondary fermentation and methanogenesis. If this was not the case, there would at some point emerge a terminal accumulation of dry solids (DS), volatile solids (VS) or fermentation products such as various fatty acids, and gas production would have seized. Thus, the material from this reactor is a perfect starting point for the following induction steps as it has no "memory" of the original substrate. Furthermore, the reactor material does no longer contain any disturbing substances such as proteins, fats, sugars, DNA, particulate matter etc, other than what can be derived from the microbial population, that can influence the subsequent steps in the rational enzyme mining. That is, when the content in the container is stable and the production of metabolites and end products of the microbial community are at a steady-state, a nullified reactor has been reached, which occurred after approx. 5 months after switch to defined medium (see FIG. 3A-D).

Batch Induction

Both batch bottles started producing gas immediately upon mixing of microbial population from the nullified reactor with the two defined media. This is normally not the case in standard batch experiment proceedings where a lag phase is most often noted, caused by the necessary hydrolysis of substrate and/or microbial growth. It was also found that the methane production commenced concomitantly with the gas production and that methane concentration was as high as 50% after 3 days. That is, the gas production was not only a result of fermentation but the number of methanogens was high enough to convert fermentation products to methane. Importantly, the bottle that had cellulose added to induce regulation of expression of cellulases showed a higher overall gas production (approximately 10% more) relative to the batch culture that had only been supplemented with the defined medium. Thus, this implies that the cellulose was influenced and degraded to single sugars by the microbial community, and subsequently was fermented and further converted to methane.

2-DE Sample Preparation and Gels

Figure 4A:
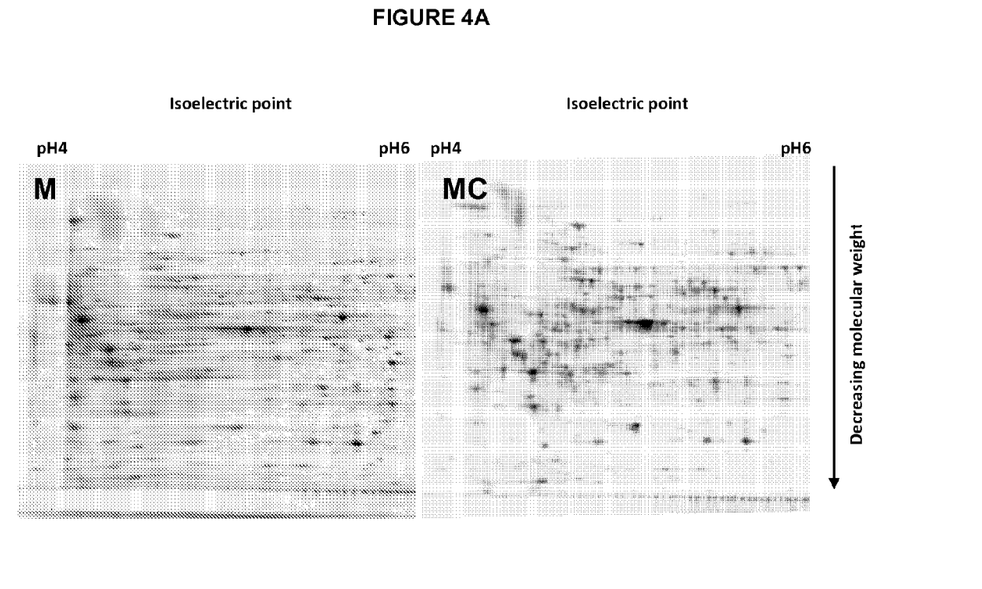
FIG. 4A. shows two 2-Dimensional Electrophoresis (2-DE) gels with a large number of protein spots at high resolution, representing the meta-secretome of the methanogenic microbial community maintained in the chemostat and collected from the liquid fraction of the two batch cultures. One culture was supplemented with defined medium and cellulose as inducing substance of interest (MC) and the other supplemented with defined medium only (M) as a reference.

The resulting two gels are presented in FIG. 4A. After sample preparation the extra-cellular proteins were concentrated by a factor 800 (volume reduction of the medium from 80.000 to 100 µl). The protein samples were further pure enough and of high enough quality and concentration to be subject to 2-DE. What is important is the fact that the extra-cellular proteins, that are present in a very diluted form in the medium, can be fractionated, purified and concentrated, and run on 2-DE gels in such a way that the gel provides protein spots of high resolution against a low background and are thus interpretable. What is further important is that both gels are similar in their protein spot pattern even though samples were not collected until 4 days after induction. This is what should be anticipated if the two batches were treated identically (besides the added inducing substrate in one of the bottles). This result is further necessary for any small differences between the two samples to be detected that would be the result from induction of protein expression regulation from a single defined substrate.

Figure 4B:
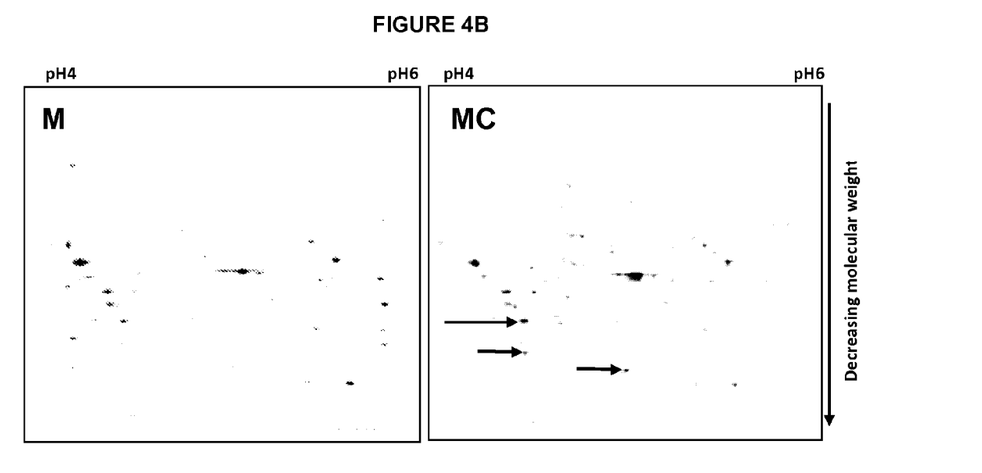
FIG. 4B shows the same gels as in 4A, after a simple image analysis (increasing brightness and contrast to the same degree). Arrows indicate proteins that have been significantly up-regulated in the culture supplemented with an inducing substance.

The methods of the present invention enables rational enzyme mining in microbial communities and the resulting gels represents the first example of a meta-secretome from an active microbial community. The gels are of high enough quality to be subjected to image analysis and identification of differences in protein expression pattern and/or expression strength between the induced and non-induced culture. Even without advanced image analysis tools it is possible to identify spots that differs in strength between the two gels (see arrows in FIG. 4B). Identified spots is then subjected to further analyses, whereas those spots that do not differ can be excluded, which dramatically will reduce the time and effort associated with cloning and screening of all the proteins.

Obviously, since the extra-cellular proteins can be fractionated, purified and concentrated to give the desired result, so can also other fractions of the cultures.

REFERENCES

1) Kirk O, Borchert T V, Fuglsang C C. Industrial enzyme applications. *Curr. Op. Biotech.*, vol. 13 (4), pp. 345-351, 2002.
2) Eijsink V G H, Bjork A, Gaseidnes S, Sirevag R, Synstad B, van den Burg B, Vriend G. Rational engineering of enzyme stability. *J. Biotech.*, vol. 13 (1-3), pp. 105-120, 2004.
3) Torsvik V, Ovreas L, Thingstad T F. Prokaryotic diversity—Magnitude, dynamics, and controlling factors. *Science*, vol. 296 (5570), pp. 1064-1066, 2002.
4) Lorenz P, Eck J. Metagenomics and industrial biotechnology. *Nature* vol. 3, pp. 510-515, 2005.
5) Bond P L and Wilmes P. The application of two-dimensional polyacrylamide gel electrophoresis and downstream analyses to a mixed community of prokaryotic microorganisms. *Environmental Microbiology*, vol. 6, pp. 911-920, 2004
6) Bond P L and Wilmes P. Metaproteomics: studying functional gene expression in microbial ecosystems. *TRENDS in Microbiology*, vol. 14, pp. 92-97, 2006.
7) Maron P-E, Ranjard L, Mougel C and Lemanceu P. Metaproteomics: A new approach for studying functional microbial ecology. *Microbial Ecology*, vol. 53, pp. 486-493, 2007.
8) Maron P-A, Cristophe M, Séverine S, Houria A, Philippe L and Lionel R. Protein extraction and fingerprinting optimization of bacterial communities in natural environment. *Microbial ecology*, vol 53, pp. 426-434, 2007.
9) Mariappan V, Vellasamy K M, Thimma J S. Identification of immunogenic proteins from *Burkholderia cepacia* secretome using proteomic analysis. *VACCINE*, vol. 28 (5), pp. 1318-1324, 2010.
10) Pocsfalvi G, Cacace G, Cuccurullo, M. Proteomic analysis of exoproteins expressed by enterotoxigenic *Staphylococcus aureus* strains. *PROTEOMICS*, vol. 8 (12), pp. 2462-2476, 2008.
11) Mould F L, Morgan R, Kliem K E and Krysttalidou E. A review and simplification of the in vitro incubation medium. *Animal feed science and Technology*, vol. 123-124, pp. 155-172, 2005.
12) Pavlostathis S G, Miller T L and Wolin M J. Fermentation of insoluble cellulose by continuous cultures of *Ruminococcus albus*. *Applied and Environmental Microbiology*, vol. 54, pp. 2655-2659, 1988.
13) Krause D O, Denman S E, Mackie R I, Morrison M, Rae A L, Attwood G T and McSweeney, C. S. Opportunities to improve fiber degradation in the rumen: microbiology, ecology, and genomics. *FEMS Microbiology Review*, vol. 27, pp. 663-693, 2003.
14) Song H, Clarke W P and Blackall L L. Concurrent microscopic observations and activity measurements of cellulose hydrolyzing and methanogenic populations during the batch anaerobic digestion of crystalline cellulose. *Biotechnology and Bioengineering*, vol. 93, pp. 369-378, 2005
15) Karlsson A, Ejlertsson J, Nezerevic D and Svensson B H. Degradation of phenol under meso- and thermophilic, anaerobic conditions. *Anaerobe*, vol. 5(1), pp. 25-35, 1999.

The invention claimed is:

1. A method for rational mining for an induced enzyme in a microbial community, comprising the steps of:
   (a) cultivating a community of microorganisms comprising at least two microbial species in at least one container in a defined culturing medium at least until the microbial community reaches a metabolic steady-state;
   (b) transferring at least one fraction from step (a) into at least two separate containers, wherein the at least two separate containers both contain a defined medium and wherein at least a first container contains an inducing substance and at least a second container does not contain the inducing substance;
   (c) cultivating the fractions from step (b), and (d) withdrawing and analyzing samples of the first and second fractions of step (c) for identification of the induced enzyme.

2. The method according to claim 1, wherein at least one container is a chemostat or an anaerobic digester.

3. The method according to claim 1, wherein the community of microorganisms originates from animals, plants, insects, soil or aqueous environments.

4. The method according to claim 1, wherein the defined medium is a medium comprising decomposed organic material, fermentation products and other essential substances.

5. The method according to claim 4, wherein the other essential substances are selected from the group consisting of salts, vitamins, metals and trace elements.

6. The method according to claim 1, wherein the content of samples taken in step (d) are separated into fractions before analyses and identification.

7. The method according to claim 1, wherein the samples taken in step (d) are subject to purification.

8. The method according to claim 7, wherein the purification is done by separation methods based on the varying physicochemical properties of proteins.

9. The method according to claim 1, wherein the samples taken in step (d) are subject to concentration.

10. The method according to claim 9, wherein the concentration is done by separation methods based on the varying physicochemical properties of proteins.

11. The method according to claim 1, wherein the analyses and identification of step (d) is done by 1 or 2 dimensional gel electrophoresis or chromatography followed by comparison of the results for the two fractions.

12. A method for rational mining for an induced enzyme in a microbial community and for production thereof, comprising the steps of:
  (a) cultivating a community of microorganisms comprising at least two microbial species in at least one container in a defined culturing medium at least until the microbial community reaches a metabolic steady-state;
  (b) transferring at least one fraction from step (a) into at least two separate containers, wherein the at least two separate containers both contain a defined medium and wherein at least a first container contains an inducing substance and at least a second container does not contain the inducing substance;
  (c) cultivating the fractions from step (b);
  (d) withdrawing and analyzing samples of the first and second fractions of step (c) for identification of the induced enzyme;
  (e) deriving the DNA sequence that codes for the enzyme; and
  (f) producing the identified enzyme in an organism.

13. The method according to claim 12, wherein at least one container is a chemostat or an anaerobic digester.

14. The method according to claim 12, wherein the community of microorganisms originates from animals, plants, insects, soil, or aqueous environments.

15. The method according to claim 12, wherein the defined medium is a medium comprising decomposed organic material, fermentation products and other essential substances.

16. The method according to claim 15, wherein the other essential substances are selected from the group consisting of salts, vitamins, metals and trace elements.

17. The method according to claim 12 wherein the content of samples taken in step (d) are separated into fractions before analyses and purification.

18. The method according to claim 12, wherein the samples taken in step (d) are subject to purification.

19. The method according to claim 18, wherein the purification is done by separation methods based on the varying physicochemical properties of proteins.

20. The method according to claim 12, wherein the samples taken in step (d) are subject to concentration.

21. The method according to claim 20, wherein the concentration is done by separation methods based on the varying physicochemical properties of proteins.

22. The method according to claim 12, wherein the analyses and identification of step (d) is done by 1 or 2 dimensional gel electrophoresis or chromatography followed by comparison of the results for the two fractions.

23. The method according to claim 22, wherein the enzyme is analyzed and classified by mass spectrometry and de-novo sequencing.

* * * * *